United States Patent [19]

Batich et al.

[11] Patent Number: 5,286,495
[45] Date of Patent: Feb. 15, 1994

[54] PROCESS FOR MICROENCAPSULATING CELLS

[75] Inventors: Chris Batich, Gainesville, Fla.; Farid Vaghefi, Foster City, Calif.

[73] Assignee: University of Florida, Gainesville, Fla.

[21] Appl. No.: 880,866

[22] Filed: May 11, 1992

[51] Int. Cl.$^5$ ............................................. A61K 9/16
[52] U.S. Cl. ................................. 424/490; 424/488; 424/499
[58] Field of Search ................... 424/490, 488, 499; 435/178

[56] References Cited

U.S. PATENT DOCUMENTS

| | | | |
|---|---|---|---|
| 2,441,729 | 12/1943 | Steinr | 426/271 |
| 4,053,627 | 10/1977 | Scher | 424/278 |
| 4,400,391 | 8/1983 | Connick, Jr. | 424/304 |
| 4,401,456 | 8/1983 | Connick | 424/488 |
| 4,767,441 | 8/1988 | Walker et al. | 71/79 |
| 4,867,984 | 9/1989 | Patel | 424/490 |
| 5,084,350 | 1/1992 | Chang et al. | 435/178 |
| 5,149,543 | 9/1992 | Cohen | 424/499 |

OTHER PUBLICATIONS

Archives of Microbiology; Allison, Milton J., Karl A. Dawson, William R. Mayberry & John Foss (1985).

Allison, Milton, J., Karl A. Dawson, William R. Mayberry, and John G. Foss (1985) "Oxalobacter formigenes gen. nov., sp. nov.: oxalate-degrading anaerobes that inhabit the gastrointestinal tract" Archives of Microbiology 141:1–7.

Merkle, H. P., and P. Speiser (1973) "Preparation and In Vitro Evaluation of Cellulose Acetate Phthalate Coacervate Microcapsules" Journal of Pharmaceutical Sciences 62(1):1444–1448.

Jacobsen, Dag, Tracy P. Hewlett, Rhonda Webb, Stephen T. Brown, Anacelto T. Odinario, Kenneth E. McMartin (1988) "Ethylene Glycol Intoxication: Evaluation of Kinetics and Crystalluria" The American Journal of Medicine 84:145–152.

Sun, Anthony M. (1988) "Microencapsulation of Pancreatic Islet Cells: A Bioartificial Endocrine Pancreas" Methods in Enzymology 137:575–580.

Bialer, M., S. A. Kaplan, and A. Yacobi (1988) "Animan Models in the Primary Screening of Controlled Release Formulations" Oral Sustained Release Formulations: Design and Evaluation pp. 183–193.

Hodgkinson, A. (1977) "Metabolism In Lower Plants" Oxalic Acid in Biology and Medicine pp. 118–125.

Hodgkinson, A. (1977) "Human and Animal Pathology" Oxalic Acid in Biology and Medicine pp. 220–223.

*Primary Examiner*—Thurman K. Page
*Assistant Examiner*—William E. Benston, Jr.
*Attorney, Agent, or Firm*—Saliwanchik & Saliwanchik

[57] ABSTRACT

Oxalate-degrading enzymes and bacteria were encapsulated for both enteric and intraperitoneal administration. We have shown that via alginate microencapsulation of *Oxalobacter formigenes*, enzymatic activity was retained for several months. A new process was developed which strengthened the alginate microcapsules and their tolerance to citrate treatment. Much smaller (30–50 μm) alginate microcapsules were made for injection as means of implantation. For oral administration, multi-encapsulated microspheres of cellulose acetate phthalate in poly-2-vinylpyridine (pKa=3.5) were prepared to protect the enzymes from gastric juices.

19 Claims, 5 Drawing Sheets

CELLULOSE ACETATE PHTHALATE

POLY 2 - VINYL - PYRIDINE (PVP)

SOLVENT EVAPORATION TECHNIQUE

PROCESS FOR MICROENCAPSULATING CELLS

DESCRIPTION

This invention was made with Government support under Grant No. NIH5PO1DK20586-14 awarded by the National Institutes of Health. The Government has certain rights in this invention.

BACKGROUND OF THE INVENTION

Microencapsulation is the process of enveloping certain drugs, enzymes, toxins, or other substances in polymeric matrices. It can be used in controlled release or delayed release of drugs. The many applications, available matrices, and techniques are extensively covered elsewhere (see, for example, Chang, T.M.S. [1977] *Biomedical applications of immobilized enzymes and proteins*, Vols. 1-2, New York: Plenum Press; Deasy, P. B. (ed.) [1984] "Microencapsulation and related drug processes," In J. Swarbrick (ed.), *Drugs and the pharmaceutical sciences*: Vol. 20. *Microencapsulation and related drug processes*, New York: Marcel Dekker, Inc.; McGinity, J. W. [1989] "Aqueous polymeric coatings for pharmaceutical dosage forms," *Drugs and the Pharmaceutical Sciences* 36; Nixon, J. R. (ed.) [1976] "Microencapsulation," In J. Swarbrick (ed.) *Drugs and the pharmaceutical sciences*: Vol. 3, New York, Marcel Dekker, Inc.).

Polymeric matrix microencapsulation of microorganisms is a relatively new technology which has potentially major implications in the treatment of various afflictions. Examples of afflictions in which treatment involving microcapsules could be advantageous are diabetes and urinary stone diseases. Insulin dependent diabetes mellitus (IDDM) is a severe disease which afflicts millions of Americans, causing substantial disruption of lifestyle and often resulting in severe health problems. The exact causes of IDDM have remained largely a mystery, despite years of intensive research on this disease. It is now widely recognized that IDDM is an autoimmune condition whereby the body's natural immunological defenses destroy the $\beta$-cells of the pancreas. $\beta$-cells are responsible for the production of insulin, and, once a substantial portion of the $\beta$-cells are destroyed, those individuals afflicted with the disease must rely on exogenous sources of insulin, usually in the form of injections. The success of pancreas or islet cell transplantations is very limited because of immune responses typically mounted by the recipient against the foreign cells.

Urolithiasis, or urinary stone disease, is a common urinary tract problem afflicting more than 10% of the U.S. population. Urinary tract stones are usually classified according to their composition, with the most frequently encountered (70%) being the calcium stone composed of calcium oxalate alone or calcium oxalate mixed with calcium phosphate. Although precipitation of calcium oxalate depends on a urine saturated with both calcium and oxalate ions in a metastable state, it has been argued that the oxalate ion concentration is more significant in the formation of urinary calcium oxalate stones. Thus, the management of oxalate in individuals susceptible to urolithiasis would seem especially important. The majority of oxalate in plasma and urine is derived from the endogenous metabolism of ascorbic acid, glyoxylate, and to a lesser degree, tryptophan. In addition, between 10% and 20% of the urinary oxalate is absorbed from the diet, especially through ingestion of leafy vegetables and plant materials, although there is disagreement in the literature about the relative amounts of diet and endogenous oxalate. Ingestion of ethylene glycol, diethylene glycol, xylitol, and excess ascorbic acid can lead through metabolic conversions to disorders of excess oxalate. Use of methoxyflurane as an anaesthetic can also lead to oxalosis. Aspergillosis, infection with an oxalate-producing fungus, can lead to production and deposition of calcium oxalate. Other causes of excess oxalic acid include renal failure and intestinal disease.

It is believed that lowering the oxalate levels in the plasma, and subsequently the urine, would decrease the incidence of calcium oxalate stone formation. Unfortunately, there are no known naturally occurring oxalate degrading or metabolizing enzymes in vertebrates. Catabolism of oxalic acid appears restricted to the plant kingdom.

Hyperoxaluria can also be related to genetic disorders. Primary hyperoxaluria is a general term for an inherited disorder which reveals itself in childhood and progresses to renal failure and frequently death in adolescence. It is characterized by high urinary excretion of oxalate and recurring calcium oxalate kidney stones. Primary hyperoxalurias consist of two rare disorders of glyoxylate and hydroxypuruvate metabolism. There are no satisfactory treatments for the two types of primary hyperoxaluria. Hemodialysis and renal transplantation have not been successful in halting the progress of this disease. Controlled diet has also failed to stop the complications of primary hyperoxaluria. Primary hyperoxaluria eventually leads to other abnormalities such as urolithiasis, nephrocalcinosis with renal failure, systemic oxalosis, and oxalemia.

Oxalate toxicity can also cause livestock poisoning, due to grazing on oxalate-rich pastures. Ingestion of oxalate-rich plants such as *Halogeton glomeratus, Bassia hyssopifolia, Oxalis pes-caprae,* and *Setaria sphacelata*, or grains infected with the oxalate-producing fungi *Aspergillus niger*, has been reported to cause oxalate poisoning in sheep and cattle. Chronic poisoning is often accompanied by appetite loss and renal impairment. Acute toxicity can lead to tetany, coma, and death (Hodgkinson, A. [1977] *Oxalic acid in biology and medicine*, London: Academic Press, pp. 220-222).

Three mechanisms for oxalate catabolism are known: oxidation, decarboxylation, and activation followed by decarboxylation (Hodgkinson, A. [1977], supra at 119-124). Oxalate oxidases are enzymes that are found in mosses, higher plants, and possibly fungi which catalyze the oxidation of oxalate to hydrogen peroxide plus carbon dioxide: $(COOH)_2 + O_2 \rightarrow 2CO_2 + H_2O_2$. Oxalate decarboxylases are enzymes which produce $CO_2$ and formate as products of oxalate degradation. An $O_2$-dependent oxalate decarboxylase found in fungi catalyzes the decarboxylation of oxalic acid to yield stoichiometric quantities of formic acid and $CO_2$: $(COOH)_2 \rightarrow CO_2 + HCOOH$. Varieties of both aerobic and anaerobic bacteria can also degrade oxalic acid. An activation and decarboxylation mechanism is used for degradation of oxalate in *Pseudomonas oxalaticus* and other bacteria. The many pathways leading to oxalate are discussed elsewhere (Hodgkinson, A. [1977] supra; Jacobsen, D. et al. [1988] *American Journal of Medicine* 84:145-152).

*Oxalobacter formigenes* is a recently described oxalate-degrading anaerobic bacterium which inhabits the rumen of animals as well as the colon of man (Allison, M. J. [1985] *Arch. Microbiol.* 141:1-7). *O. formigenes* OxB is a strain that grows in media containing oxalate as the sole metabolic substrate. Other substrates do not appear to support its growth. The degradation of oxalate catalyzed by the bacterial enzyme results in $CO_2$ and formic acid production (Allison [1985], supra).

Recently, research has focused on matrices used to encapsulate cells and organisms. The use of alginate gel technology to formulate agricultural products, pesticides, and food items has been disclosed. For example, U.S. Pat. No. 4,053,627 describes the use of alginate gel discs for mosquito control; U.S. Pat. No. 3,649,239 discloses fertilizer compositions; and U.S. Pat. No. 2,441,729 teaches the use of alginate gels as insecticidal as well as candy jellies. In addition, U.S. Pat. Nos. 4,401,456 and 4,400,391 disclose processes for preparing alginate gel beads containing bioactive materials, and U.S. Pat. No. 4,767,441 teaches the use of living fungi as an active material incorporated in an alginate matrix.

The most usual hydroxyl polymers used for encapsulating biomaterials are alginate, polyacrylamide, carrageenan, agar, or agarose. Of these, alginate and carrageenan are the only ones which can be manufactured simply in spherical form with encapsulated material. This is done by ionotropic gelling, i.e., the alginate is dropped down into a calcium solution and the carrageenan into a potassium solution. However, the resulting beads are stable only in the presence of ions (calcium and potassium, respectively).

The use of ultrasonic nozzles has offered a new way of making smaller microspheres with very good control over the size of the droplets (Ghebre-Sellassie, I. [1989] "Pharmaceutical pelletization technology," In J. Swarbrick (ed.) *Drugs and the pharmaceutical sciences*: Vol. 37. *Pharmaceutical pelletization technology*, New York: Marcel Dekker). Liquid is supplied at low pressure and droplets are formed at the tip of the nozzle by ultrasonic frequency. However, it has not been possible to atomize the higher viscosity alginates.

Cellulose acetate phthalate (CAP) is a polyelectrolyte containing ionizable carboxyl groups. It is an enteric coating widely used in the industry for coating tablets. Enteric coatings protect the drug from the gastric juices (pH range 1-6) (Yacobi, A., E. H. Walega [1988] *Oral sustained release formulations: Dosing and evaluation*, Pergammon Press). CAP serves this purpose by being virtually insoluble below pH 6.0. Aquateric is a commercially available pseudolatex with CAP content of $\approx 70\%$. Other constituents include Pluronic F-68, Myvacet 9-40, polysorbate 60 and $\leq 4\%$ free phthalic acid (McGinity [1989], supra). Both CAP and aquateric can be fabricated into microspheres by first dissolving them in pH 7.0 distilled deionized water and dropped in acidic solution (Madan, P. L., S. R. Shanbhag [1978] *Communications, J. Pharmac.* 30:65). Others have used coacervation as the method for microencapsulation (Merkle, H. P., P. Speiser [1973] *J. Pharmac. Sci.* 62:1444-1448).

The use of various matrices to encapsulate cells and organisms for implantation in the body has been previously reported (Sun, A. M. [1988] "Microencapsulation of pancreatic islet cells: A bioartificial endocrine pancreas," In Mosbach, K. (ed.) *Methods in enzymology:* Vol. 137, Academic Press, Inc.). Pancreatic cells have been utilized in vitro and in vivo for the production and delivery of insulin. Long term in vivo (in rats) studies of alginate microcapsules containing islet cells, implanted in the peritoneal cavity, have shown great biocompatibility with no cell adhesion to the capsules and a reversal to normal of the previously diagnosed diabetic rats (Sun, A. M., Z. Cai, Z. Shi, F. Ma, G. M. O'Shea [1987] *Biomaterials, Artificial Cells, and Artificial Organs* 15(2):483-496).

In vitro cell cultures of hybridomas are now routinely utilized for the preparation of monoclonal antibodies of great specificity. Cancer cell lines are used in vitro for formation of such hybridomas, and also for the screening and testing of potential carcinogenic and anticarcinogenic compounds. Also, the industrial utilization of isolated immobilized cells has received attention, since these can be used as catalysts for biochemical reactions, and such reactions can be used as important tools in syntheses and analytical determinations.

In many instances, the direct introduction of a foreign cell into a host can produce severe immune response in the host. For example, when growing hybridoma cells in the ascites fluid of a host such as a mouse, the mouse has to be pretreated to prevent immune response. When injecting whole islet cells into a human, immune response is also a complicating factor. A need therefore exists for improved methods of facilitating the introduction of such cells into a host, as well as generally for facilitating the manipulation of cells in vitro. The problems confronted by the practitioner in attempting to extend many of the prior art techniques to the encapsulation of living cells or other sensitive biomaterial are numerous. Many of the existing techniques operate under conditions which are too drastic for the survival or continuing viability of a living cell, or cause degradation of the biomaterial desired to be encapsulated. For example, the use of organic solvents, high temperatures, reactive monomers, cross linking conditions, and the like, may hamper the viability or otherwise degrade the biomaterial to be encapsulated. Moreover, it is crucial to prevent dehydration or osmotic rupture of the cell. Another serious problem is the necessity of providing the microcapsule walls with sufficient permeability for nutrients, and secretion and excretion products, to pass through, yet prevent the entry of molecules or cells of a host, for example, products of the host's immune response, which could destroy the encapsulated material. A further complicating factor is the need to provide sufficient structural integrity of the capsule while keeping the above considerations in mind. Prior art methods of alginate encapsulation, while gentle to the encapsulated material, have failed to produce a capsule of sufficient strength to maintain structural integrity over a long period of time.

A need therefore continues to exist for a method to encapsulate living cells and other sensitive biomaterial under sufficiently mild conditions which allow the cells or biomaterial to remain substantially unaffected by the encapsulation process, yet which also allow the formation of a capsule of sufficient strength to exist over long periods of time.

BRIEF SUMMARY OF THE INVENTION

The subject invention relates to materials and methods for immobilizing biomaterial such as animal or plant cells, bacteria, algae, fungi, antibiotics or other drugs, viruses, or polypeptides by encapsulation in a polymeric matrix. In accordance with the teachings of the subject invention, sensitive biomaterial can be encapsulated with full viability and with retained growth ability.

The compositions and methods of the subject invention are illustrated herein with reference to encapsulation of certain bacteria. Bacteria which produce a useful product can be encapsulated and introduced into a human or other animal. The encapsulation of bacteria is specifically exemplified herein by the encapsulation of *Oxalobacter formigenes*. The encapsulated *O. formigenes* can be introduced into a human or animal and the bacteria continue to produce and release enzyme but are not subject to attack from the immune system.

In specific embodiments of the subject invention, oxalate-decomposing bacteria and enzymes can be successfully encapsulated in either alginate microcapsules or cellulose acetate phthalate (CAP) microspheres. Procedures using CAP encapsulation techniques to coat materials such as aspirin and antibiotics for enteric use are also described. Viability tests of the encapsulated biomaterials exhibited activity after encapsulation in either alginate or CAP. For enteric administration, double-encapsulation of CAP in polyvinylpyridine (PVP) can be utilized to ensure total protection of the enzyme from food substances and through the gastric region. This also eliminates the need for force feeding animals, for example, during the course of the in vivo studies. One aspect of the invention is the discovery of a procedure for affecting this double encapsulation. Specifically, by dissolving PVP in methylene chloride, it is possible to coat CAP microspheres.

Long term studies demonstrated enzyme activity after two months at 37° C. for alginate encapsulated *Oxalobacter formigenes*. Limitations on bacterial loads were eliminated by reinforcing the shell with alternating layers of pure alginate and poly-L-lysine (PLL). Therefore, therapeutic dosage rates of *Oxalobacter formigenes* can now be encapsulated.

A further aspect of the subject invention is a procedure for forming small alginate microcapsules of about 30-50 μm. The droplets can be formed using, for example, an ultrasonic nozzle and, according to the subject invention, their entry into a gelling solution can be facilitated by the use of a surfactant and by imparting a surface charge to these droplets.

DETAILED DISCLOSURE OF THE INVENTION

The subject invention concerns novel materials and methods for microencapsulation of biological materials. For example, islet cells or bacteria can be encapsulated according to the procedures of the subject invention. The encapsulation structures produced according to the subject invention have greatly enhanced stability so that these microcapsules can maintain their structural integrity for long periods of time.

In one embodiment of the invention, the enhanced structural stability of the encapsulated cell arises as the result of an improvement over traditional alginate microencapsulation procedures wherein the improvement comprises coating the surface of poly-L-lysine (PLL) treated alginate microcapsules with several layers of pure (bacteria-free) alginate and additionally complexed with more lysine before a final liquefaction step (citrate treatment, for example).

Figure 1:
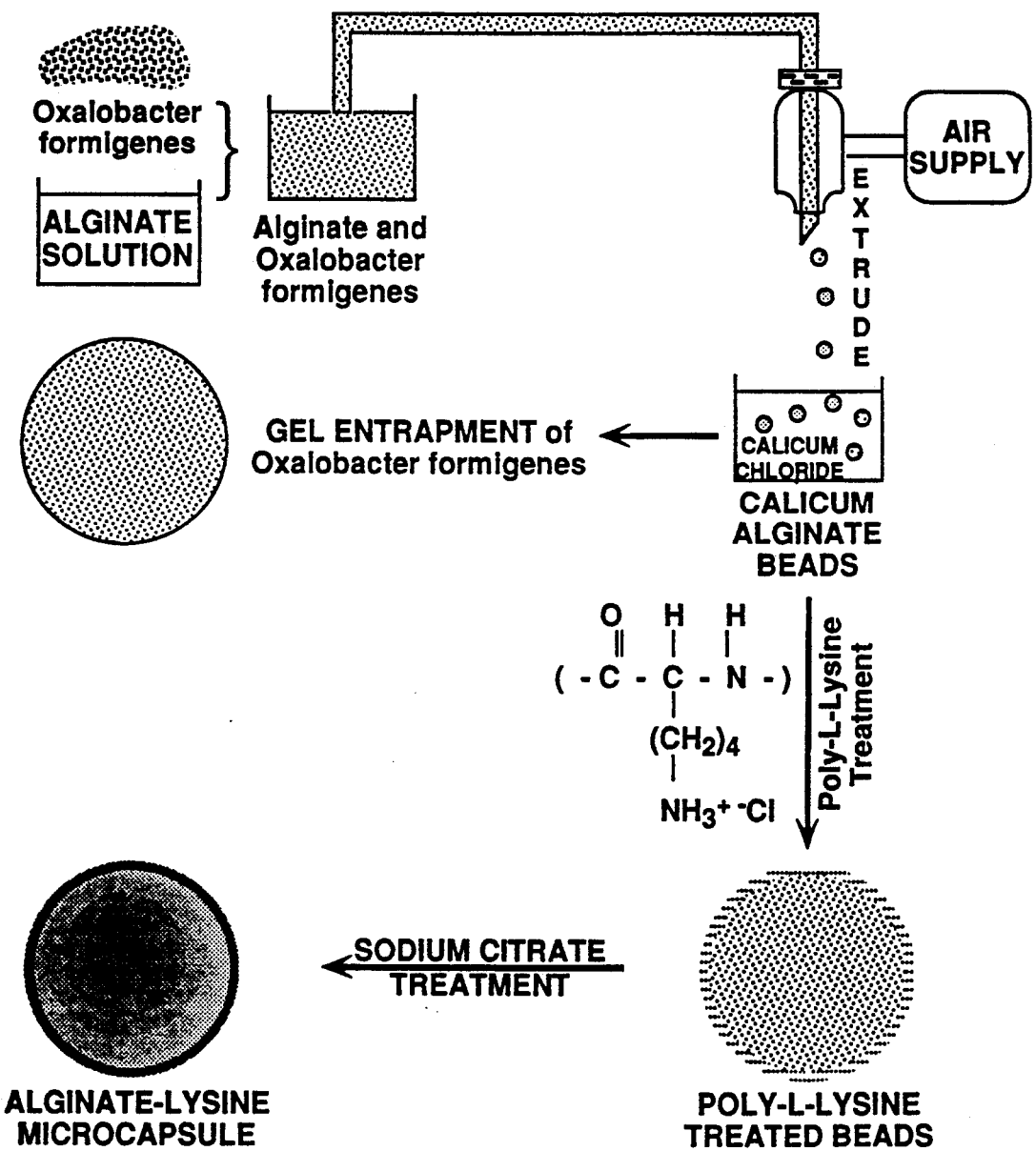
FIG. 1 is a schematic illustration of alginate encapsulation using a double-barrel coextrusion nozzle. Droplets at the end of the nozzle are blown off the needle tip by the coaxial air stream and collected in calcium chloride solution.

A standard procedure for producing alginate microcapsules is shown in FIG. 1. Bacteria or other cells are initially placed in an alginate solution. Droplets from this mixture are then introduced into a solution comprising metal ions which stabilize the alginate layer. Metal cations that react with and cause gelation (stabilization) of sodium alginate solutions are, for example, the cations of calcium, barium, zinc, copper, aluminum, and mixtures of these. A water soluble calcium salt such as calcium chloride is generally preferred for the process of this invention because it is usually non-toxic to living cells. An effective concentration range of calcium dichloride gellant bath, also called the salt solution or gelling solution, is 1% to 15% (w/v), but 2% to 5% is preferred. Gelation proceeds further as the concentration of the salt solution is increased.

There are a variety of methods known in the art for introducing the alginate mixture into the calcium chloride solution. Preferably, the method used will create droplets of appropriate size which are then introduced to an appropriate depth into the gelling solution. For example, appropriate droplets can be made using an apparatus which has a double lumen drop former (Sefton, M. V., R. M. Dawson, R. L. Broughton [1987] *Biotechnology and Bioengineering* 29:1135-1143). Air is driven through the outer lumen and the polymer solution is flow-regulated through a syringe-tip inner lumen.

Figure 2:
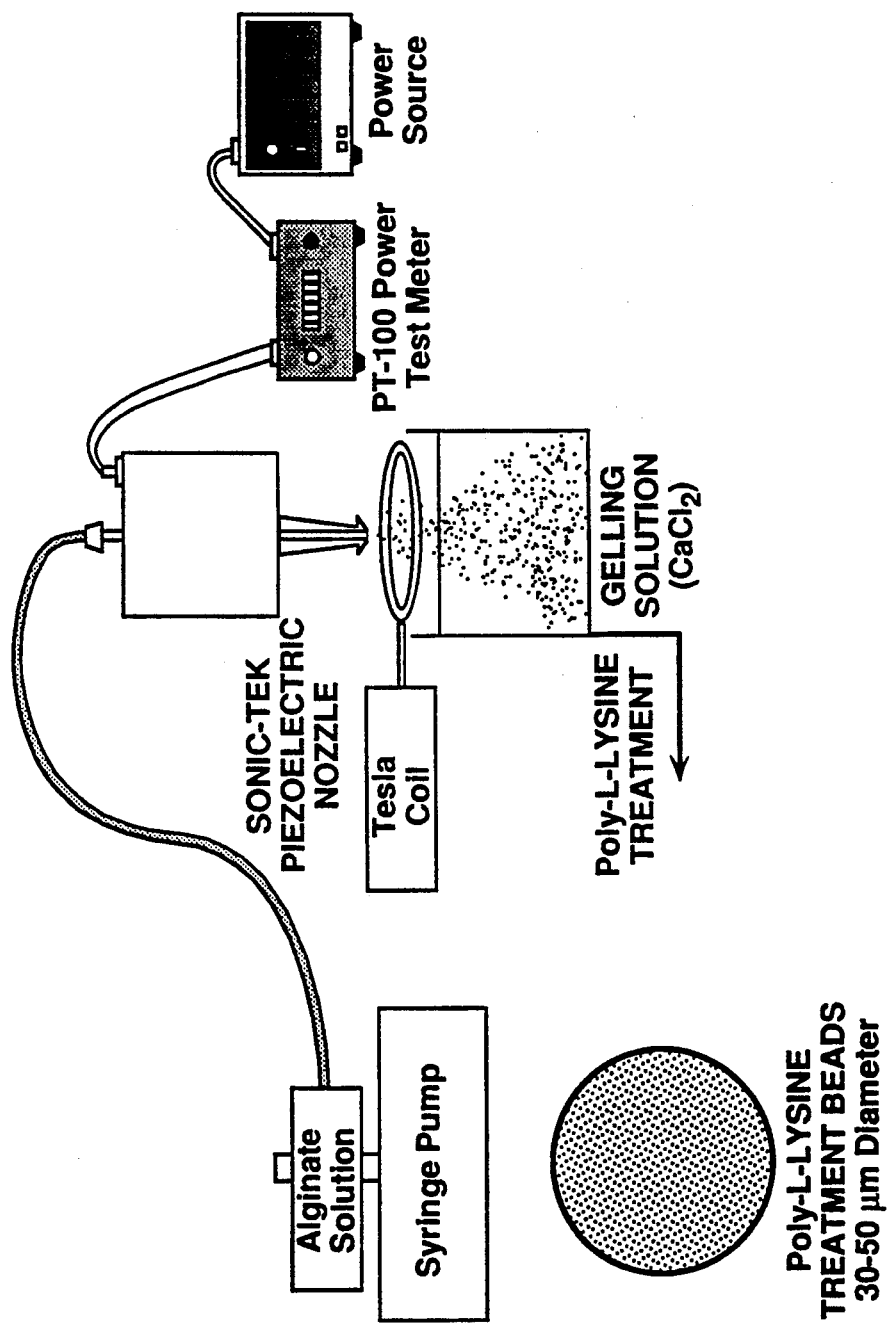
FIG. 2 shows piezoelectric sonication of Keltone LV to make microcapsules of 30-50 μm in diameter.

One aspect of the invention is the use of piezoelectric techniques for droplet formation combined with electrostatic charging of the droplets as the droplets fall towards the gelling solution. This technique is preferably combined with the use of surfactants, as described herein, which help the very small droplets to enter the gelling solution to an appropriate depth. Advantageously, as described in detail herein, a tesla coil can be utilized to impart the necessary charge on the droplets before the droplets enter the gelling solution (see FIG. 2). After immersion in the gelling solution, the microcapsules can be removed from the solution and treated with a solution of a positively charged polyelectrolyte such as poly-L-lysine (PLL). Typically, a final step in the process of making alginate microspheres involves removal of the calcium ions by, for example, treatment with sodium citrate. This step essentially liquefies the interior of the microcapsule leaving a thin alginate-lysine membrane surrounding the cells which are then in a fluid environment.

In addition to the use of electrostatic charging techniques to facilitate the entry of very small droplets into the gelling solution, a further aspect of the invention is the production of highly stable microcapsules by adding layers of pure alginate and poly-L-lysine before the liquefaction step. Thus, in a preferred embodiment of the subject invention, alginate microcapsules which have already been treated with PLL are dipped into a pure alginate solution (no bacteria) and rinsed with saline. The alginate solution at this step is typically diluted to about 10% of the concentration of the original alginate solution. Isotonic saline can be used to make this dilution. The original alginate solution is typically about 0.5% to about 2.5% and, preferably, about 1.6%. Thus, the concentration of the second alginate solution can be about 0.05% to about 0.25% and, preferably, about 0.16%. These concentrations can be varied by a person skilled in this art, using the teachings provided herein, to produce microcapsules having the desired properties. The concentrations may be varied, for example, to take into account different molecular weights of the alginate solutions. Preferably, the microcapsules are dipped in the alginate solution for about 2 minutes. Once the microcapsules are removed from the alginate dip, they are then dipped in a poly-L-lysine solution. The concentration of the poly-L-lysine solutions can be, for example, from about 0.05% to about 0.3% and, preferably, from about 0.1% to about 0.2%. Preferably, the poly-L-lysine dip is for about 2 minutes. In a preferred embodiment of the invention, the alginate and poly-L-lysine dips are repeated about 3 times. In a preferred embodiment of the invention, the alginate dip is performed last to ensure a biocompatible surface.

There are several variables which can be manipulated to achieve desired alginate properties (permeability, membrane thickness, and toughness). These variables, which are listed in Table 1, include poly-L-lysine and alginate molecular weight, concentration, and treatment time. The higher the poly-L-lysine MW, the weaker the microcapsules, since the diffusion into the alginate is limited. Besides using lower molecular weight poly-L-lysine, higher concentration and longer treatment time can be used to increase strength.

lower calcium content of the Keltone LV (0.2% compared to 1.2% for Kelmar) could be responsible for the lower viscosity.

There is a weakening effect (more ruptured microcapsules present) as the bacterial load in the capsules is increased. The limit was reached at a load of 20 mg of bacteria/ml of 1.6% Keltone LV solution, at which limit capsules of spherical shape and moderate strength were impossible to make. Even at 10 mg/ml, the capsules had a small tail and could not be treated with citrate.

By encapsulation in a permeable polymeric matrix (such as alginate), organisms such as islet cells or *Oxalobacter formigenes* (an oxalate-degrading bacteria), are isolated from the body's immune response. At the same time, the body is protected from the toxic effects of the bacteria. The matrix is totally impermeable to large molecules such as immunoglobulins. Meanwhile, smaller molecules such as glucose or oxalate and their byproducts, freely diffuse in and out of the protective shell.

In one embodiment of the subject invention, we encapsulate *Oxalobacter formigenes* in a polymer matrix which is inert in the peritoneal cavity. The matrix must be biocompatible and permeable to oxalate and its byproducts while keeping the bacteria safe from the body's immune response. An ionic gelatin procedure using potassium alginate and poly-L-lysine was used. The alginates were purchased from Kelco Inc.; and poly-L-lysines (22, 130, 190, 230 kD MW) were purchased from Sigma Chemical Company. A bacteria-alginate mixture was made for microencapsulation. The procedure involved complexing alginate with calcium ions to form a gel. These microspheres were then

TABLE 1

Summary of variables affecting alginate microcapsule properties.
PARAMETERS IN ALGINATE MICROENCAPSULATION

| Parameter | CHANGE | MEASUREMENT PROPERTY | | |
| --- | --- | --- | --- | --- |
| Manipulated | Higher/Lower | Permeability | Toughness | Shell thickness |
| Alginate | Molecular weight | Larger MW | Decreased | Increased | Decreased |
| Bacteria load | mg bacteria/ml alginate | Larger load | N/A | Decreased | N/A |
| Poly-L-lysine | Molecular weight | Larger MW | Increased | Decreased | Increased |
| Citrate treatment | Treatment time | Longer time | Increased | Decreased | No effect |

These parameters, and others listed above, can be modified by a person skilled in this art using the teachings provided herein to vary shell thickness, permeability, texture, and toughness of the resulting microcapsules.

Kelmar and Keltone are two commonly available alginate preparations. Kelmar (0.8 and 1.6%) and Keltone LV (1.6 and 1.8%) were tested for their properties with respect to the production of microcapsules. The capsules did not show any distinguishable difference other than their solution viscosity. Although the higher viscosity Kelmar is expected to yield a tougher shell (Thies, C. [1987] *How to make microcapsules: Ionic gelation*, Washington University, Biological Transport Laboratory, pp. 1-25), we found Keltone LV to be the preferable alternative for processing reasons. The 1.6% Kelmar (120-150 kD MW) was very viscous (1390 cps) and extrusion through <22 gauge needle was possible only at very low flow rates (<2 ml/hour). The 0.8% Kelmar provides faster extrusion but a weaker capsule with less toleration to the citrate treatment. The Keltone LV (50-80 kD MW) proved to be the better alternative with easier processibility and good capsular strength. Other than the lower molecular weight, the treated with poly-L-lysine to form a more durable outer shell. These microspheres were transformed into microcapsules by using 1.5% w/v isotonic citrate buffer to liquify the calcium-alginate core.

The capsules of the subject invention are especially useful for the administration of cells to an animal, wherein the immune response of the animal towards the cell is to be minimized. Thus, hybridoma cells can be grown in an animal by injecting capsules comprising said cells into the animal. Drug delivery to an animal can be greatly facilitated by injecting the animal with capsules comprising cells which produce a pharmacologically active agent. Thus, recombinant bacteria which produce insulin, growth hormone, or interferon, for example, could be injected into an animal to proved a ready and continuous source of these active agents. Encapsulated pancreatic cells could be injected into a diabetic subject so as to provide a ready source of insulin. Cells which produce antibodies, enzymes, and other bioactive materials can also be administered. The tough shell and small size of the capsules of the subject invention facilitate administration of the microcapsules by injection.

The administration of the capsules could be by local administration, orally, or parenterally.

Alternatively, the capsules of the subject invention have other uses. For example, they can serve as catalytic materials in place of the heretofore used immobilized microbial cells or immobilized enzymes. They can be used for analytical purposes, for example, by utilizing degradative encapsulated microorganisms to release a product such as oxygen, which can then be monitored by means of an oxygen electrode, as is well known in the art.

When the microcapsules are used therapeutically, the amount to be provided to the subject will depend on the age, sex, size, condition of the subject, other concurrent administration, contraindications, and the like. For example, it is readily calculable, for a given application, how much insulin should be released into the system over a given period of time, and accordingly the appropriate amount of encapsulated cells to administer.

In another embodiment of the invention, cells, drugs, or other materials can be treated with cellulose acetate phthalate (CAP) for enteric use. An important aspect of the subject invention is the discovery of a process for coating materials with both CAP and polyvinylpyridine (PVP). This combined coating is highly advantageous for materials which are to be administered as part of a food substance and, in particular, as part of a food substance with a high moisture content. The double coating is necessary because CAP, which withstands the highly acidic gastric environment, dissolves in neutral pHs such as those of baby food or animal food pastes. By coating CAP microspheres with PVP, we have created microspheres resistant to both the neutral pHs of foodstuffs as well as the acidic environment of the stomach.

Following are examples which illustrate procedures, including the best mode, for practicing the invention. These examples should not be construed as limiting. All percentages are by weight and all solvent mixture proportions are by volume unless otherwise noted.

EXAMPLE 1

Microencapsulation Procedure

A 1.6 weight percent (wt. %) solution of alginate was prepared by dissolving 1.6 grams of Keltone LV (Kelco Inc., San Diego, Calif.) in 100 ml isotonic saline (Celline, Fisher Scientific). The *Oxalobacter formigenes* bacteria was dispersed in 10 ml of the 1.6 wt. % alginate solution. The bacteria content (load) was varied between 0.5 mg/ml to 10 mg/ml of alginate. The values reported are based on dry weight of the bacteria. The bacteria was lyophilized prior to encapsulation. The dry bacteria weighs $\approx \frac{1}{4}$ the wet, unlyophilized bacteria.

A 200 ml solution of 1.4 wt. % $CaCl_2$ was prepared and buffered with 13 mM HEPES to pH 7.2. The alginate/bacteria suspension was extruded through the inner lumen of a double device into the stirred $CaCl_2$ solution. Alginate extrusion rate of 12 ml/hour through a 22 gauge (22 G) needle gave the best results. The outer lumen gas flow rate was set at 3 liters/minute to form microspheres and provide a drop fall distance of 9.0 centimeters. These conditions resulted in spherical (little or no tail formation) microspheres with an average diameter of about 700 μm with very narrow size distribution (675-725 diameter size). The bead slurry (about 10 ml) was transferred into a filtration unit using a 420 micron Teflon mesh as the filter. This allowed for rapid drainage of solution for timed treatments of the microcapsules. The bead slurry was washed twice with 20 ml of isotonic saline solution. Then the beads were treated with 20 ml of 0.1 wt. % poly-L-lysine (22 kD MW, Sigma) in saline. After five minutes the solution was drained. The alginate microspheres were then treated for five minutes with 20 ml of 0.2% CHES in saline. After decanting the CHES the beads were treated with 20 ml of a diluted alginate solution (about 1/10 the concentration of the extruded alginate, 0.16% Keltone LV). The beads were washed with isotonic saline solution before the liquefaction treatment. The beads were suspended in 1.5% sodium citrate in 0.45% saline for five minutes. Finally, the microcapsules were washed and stored in isotonic saline solution at 4° C. for future use.

EXAMPLE 2

Surface Modification of Alginate Microcapsules

The surface of the alginate microcapsules containing bacteria was coated with more alternating layers of pure alginate and poly-L-lysine (PLL). This yielded a stronger shell that could withstand the 1.5% citrate treatment for longer periods. The following procedure was performed before the citrate treatment:
1. The microencapsulation procedure was performed without the citrate treatment.
2. Prepared a 0.16% Kelmar solution.
3. Prepared 50 ml of 0.2% PLL solution using a combination of different MW poly-L-lysines (total 100 mg PLL in 50 ml of isotonic saline solution):
   a. 25 mg of PLL, MW=22,400
   b. 25 mg of PLL, MW=40,750
   c. 25 mg of PLL, MW=100,500
   d. 25 mg of PLL, MW=289,000
4. Dipped the microcapsules in the PLL solution for two minutes, removed PLL and washed with saline.
5. Dipped the microcapsules in 0.16% Kelmar for two minutes, washing with isotonic saline solution after removal.
6. Repeated steps 4 and 5 three times. The alginate dipping was done last to ensure a biocompatible surface, since exposed PLL sites may cause an inflammatory response.
7. The citrate treatment was performed.

Alginate microcapsules coated with this procedure showed greater tolerance. Microcapsules having a bacteria content of 0.5 mg/ml withstood citrate treatment longer than 45 minutes with no signs of weakening or rupture. Without this coating process, capsules ruptured within 45 seconds of the citrate treatment.

This process was needed since capsular breakage was observed during citrate treatment when bacteria was incorporated. Also, severe limits were imposed on the bacteria load by the more frequent ruptures as the load concentrations were increased. This procedure offered several benefits:
1. Alginate microcapsules coated with this procedure showed greater tolerance to citrate treatment.
2. Larger bacteria loads (>1 mg bacteria/ml alginate solution) can be encapsulated to meet therapeutic dosage rates of oxalate-degrading enzymes required to offset hyperoxaluria.
3. Using different combinations of poly-L-lysines, microcapsule permeability can be customized.
4. The surface is covered with several layers of pure alginate to prevent any inflammatory response due to exposed bacteria sites.

5. The tougher shell may reduce capsular rupture during injection.

This procedure is essential for microcapsule survival in vivo. The treated alginate microcapsules (0.5 mg bacteria/ml 1.6% Keltone LV solution) withstood citrate treatments longer than 45 minutes without developing leaks. However, the untreated capsules of the same batch leaked 45 seconds after adding the citrate.

EXAMPLE 3
Poly-L-Lysine Membrane Thickness of Alginate Microcapsules

Several techniques were attempted to find the thickness of the poly-L-lysine-alginate membrane. Alginate has a water content of ≈93% (w/w, Goosen, M. F. A., G. M. O'Shea, H. M. Gharapetian [1985] *Biotechnology and Bioengineering* 27:146–150). Any drying distorted the shape and size of the capsules and resulted in a shrunken mass of solid material. Even lyophilization and critical point drying caused distortion. Immobilization of the capsules in gelatin was not successful. Finally, freezing the capsules and slicing them with a microtome showed cross sections of the capsules. The cross sections showed no or minute change in membrane thickness in respect to poly-L-lysine treatment time between 10 and 15 minutes. Our final arrangement of 0.1% w/v of 22.8 kD poly-L-lysine for 10 minutes showed a thickness of 30–40 μm.

EXAMPLE 4
Piezoelectric Sonication of Alginate and Electrostatic Charging of Droplets It was desired to make smaller alginate microcapsules. With the piezoelectric sonicating nozzle (FIG. 2), droplets of 30 μm diameter were formed using 1.6% w/v Keltone LV. However, these droplets did not enter the calcium chloride solution and instead coated the surface as a film. Several nonionic surfactants were used to solve this problem. But, surfactant concentrations as high as 10% did not prevent the film formation.

To keep the droplets separate long enough to penetrate the gelling solution, some means of surface modification was needed. Electrostatic surface charging was chosen for this purpose. Using a tesla coil as the power source, a high voltage electric field was formed to charge the surface of the droplets. Droplets of alginate were sonicated through an O-ring attached to the tesla coil and into the calcium chloride solution (see FIG. 2). As a person skilled in the art would recognize, a variety of sources of an electrified field could be utilized to impart the surface charge to the droplets. We used a "Vacuum Lock Detector" as described at page 1287 of 1991-1992 Fisher Scientific catalog. This instrument was connected to an O-ring as described herein. Using this approach, alginate microcapsules of 35 μm average diameter were made.

The following parameters can be used:
1. Nozzle to metal O-ring distance of 3.2 cm (O-ring was attached to tesla coil and situated directly under the nozzle).
2. O-ring to $CaCl_2$ solution distance of 1.8 cm.
3. A 2.0% v/v solution of TWEEN®20 in $CaCl_2$ (1.37%).
4. 12 ml/hour of alginate pumped through the nozzle.
5. Atomizer power source set to 4.3 watts.
6. 1.6% Keltone LV alginate solution.

Increasing the alginate pump rate is recommended as a means to achieve better size distribution of microcapsules. Also, a new filtration technique was developed to ensure proper timing of the treatments. The capsules were centrifuged at 750 rpm for five minutes and the supernatant decanted. By this procedure, it was possible to collect the microcapsules from solutions in time. A bacterium concentration of 0.5 mg/ml (bacteria/alginate solution) was successfully encapsulated and treated with poly-L-lysine.

In a preferred embodiment, both 2% v/v surfactant and the tesla coil are utilized for this procedure. Using this procedure enabled production of alginate at a faster rate (>12 ml/hour compared to <2.0 ml/hour with extrusion procedures).

EXAMPLE 5
Cellulose Acetate Phthalate (CAP) Microencapsulation

Microspheres were prepared by extrusion of a CAP mixture (pH 7.5) into 5.0M HCl solution containing one drop of the ionic FC-99, 25% Fluorosurfactant (3M Corp.).

Eight grams of CAP (Polysciences) was suspended in 100 ml of distilled deionized water (DDI) and dissolved by adjusting the pH to 7.5 using NaOH. The bacteria load was blended in. This solution was extruded into 200 ml of 5M HCl solution containing 1.0 ml of TWEEN®20 (Polyoxyethylene sorbitan monolaurate) and 100 μl of ARLACEL TM 20 (nonionic surfactant, Sorbitan monolaurate, ICI, Inc.). CAP extrusion rate of 12 ml/hour through a 22 G needle gave the best results. The gas flow rate was set at 3 liters/minute and a drop fall distance of 9.0 centimeters. The resulting microspheres were filtered and washed with DDI water and set under vacuum to dry.

Figure 3:
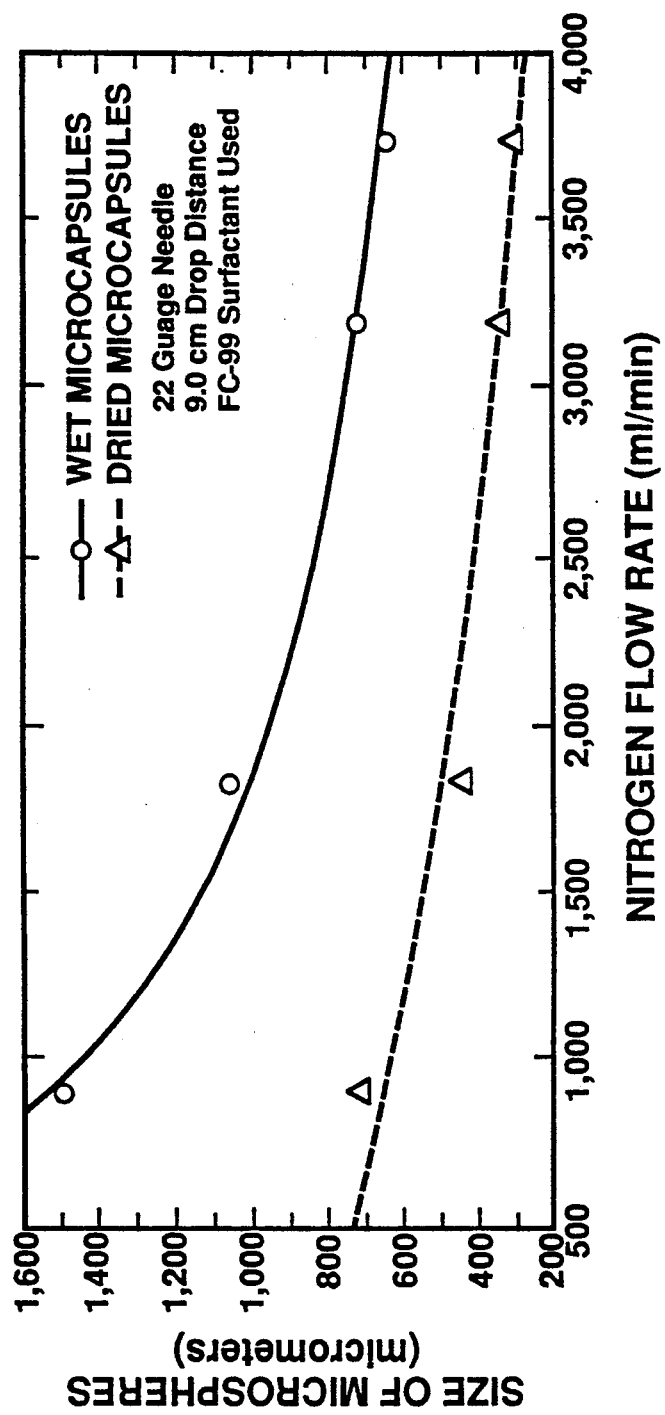
FIG. 3 demonstrates size ratio of CAP microspheres to gas flow rate. Wet and dry correspond to the shrinkage before and after drying.

Aquateric (from FMC Inc.) is an alternative CAP containing (70%) aqueous enteric coating by FMC with surfactants and plasticizers incorporated. CAP microspheres decrease in size and weight upon drying (Table 2). The results of size distribution upon varying gas flow rates is shown in FIG. 3. The gas flow rate was measured using Manostat gas flow meter. The size of the CAP microspheres was measured before and after drying. The size was determined using an Olympus optical microscope scale. Microspheres obtained at or above 4.54 l/minute had considerable deformities and a wide size distribution.

In Table 2, dry and wet sizes of two samples at each flow rate are reported. An approximately 1:2 dry:wet size ratio is observed.

TABLE 2

Size ratio of CAP microspheres to gas flow rate.

| SAMPLE STATUS | SAMPLE NUMBER | GAS FLOW (liters/minute) | | | |
|---|---|---|---|---|---|
| | | 0.9 CAP SIZE (mm) | 1.8 CAP SIZE (mm) | 3.2 CAP SIZE (mm) | 3.7 CAP SIZE (mm) |
| WET | 1 | 1.50 | 1.06 | 0.72 | 0.64 |
| | 2 | 1.46 | 1.04 | 0.70 | 0.66 |
| DRY | 1 | 0.71 | 0.44 | 0.34 | 0.31 |
| | 2 | 0.74 | 0.48 | 0.31 | 0.30 |

Shrinkage of CAP microspheres after drying
Wet/dry size ratio ≈ 2
CAP extrusion rate = 12 ml/hour
9.0 cm drop distance
22G extrusion needle

EXAMPLE 6

Piezoelectric Sonication of CAP Microspheres

A piezoelectric sonicating nozzle was used to make smaller capsules. The best results were obtained at 2.5 watts (power source) for 0.5 ml/minute liquid flow or 7.5 watts at 4.0 ml/minute of 8% CAP solution. CAP is soluble at pH greater than 6.0. By maintaining the HCl solution at less than pH 2.0, microspheres of 30 to 70 μm in diameter were obtained.

EXAMPLE 7

Tesla Coil

The use of a tesla coil and a combination of surfactants yielded CAP microspheres of 30–50 μm. The use of surfactants proved beneficial. Using a combination of TWEEN®20 and ARLACEL™ 20 (HLB values of 16.7 and 8.6, respectively) in the 5.0M HCl solution and later as a wash in water during filtration reduced agglomeration very effectively. Using water alone (no surfactants) as wash resulted in some aggregation. However, these could easily be broken down to single spheres. The use of a tesla coil was not necessary since microspheres were made without its use. However, the microspheres made using the tesla coil showed less agglomeration after drying. These microspheres proved essential for the success of the solvent evaporation technique (see Example 9). Due to the large interfacial tension, it was not possible to uniformly disperse the larger (700 μm average diameter) CAP microspheres in the PVP solution. The smaller microspheres alleviated this problem.

The use of a tesla coil allowed for higher liquid flow rate (12 ml/hour at 4.5 watts), without droplets recombining.

EXAMPLE 8

Dye Release From CAP Microspheres

The procedure above was used to make CAP microspheres with 1.25% methylene blue dye incorporated (100 mg MB/8 g CAP). Using Ultraviolet-visible (UV-Vis) spectrometer, the peak maximum for MB was determined at 663 nanometers. Dye release was examined (FIG. 4) at pH 1.45 and 7.00 by placing 1.2 mg of CAP microspheres in 1 ml cuvettes. Absorbance was recorded at 663 nanometers for up to 20 minutes.

Figure 4:
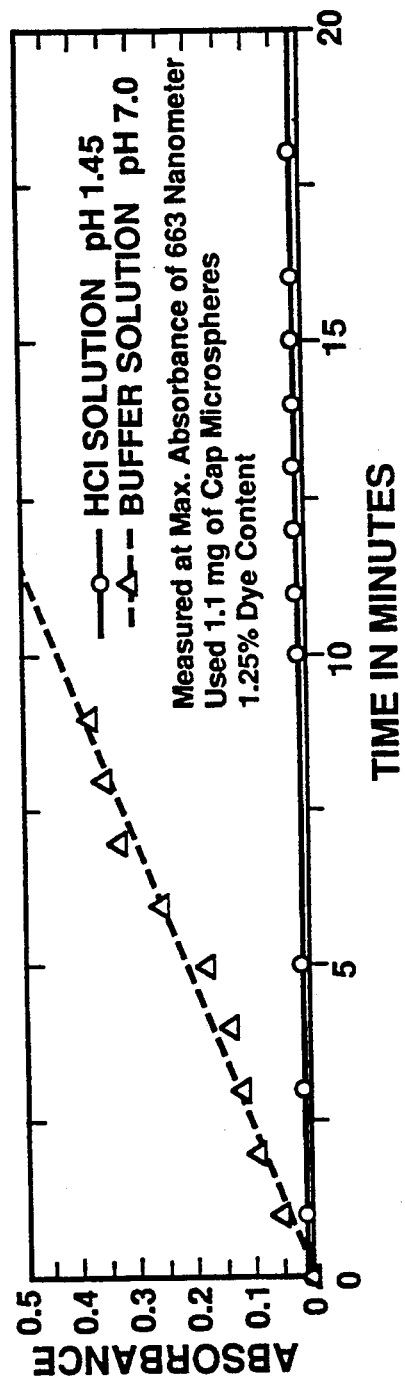
FIG. 4 shows dye (MB) release from CAP microspheres at pH 1.45 and 7.0.
Figure 5:
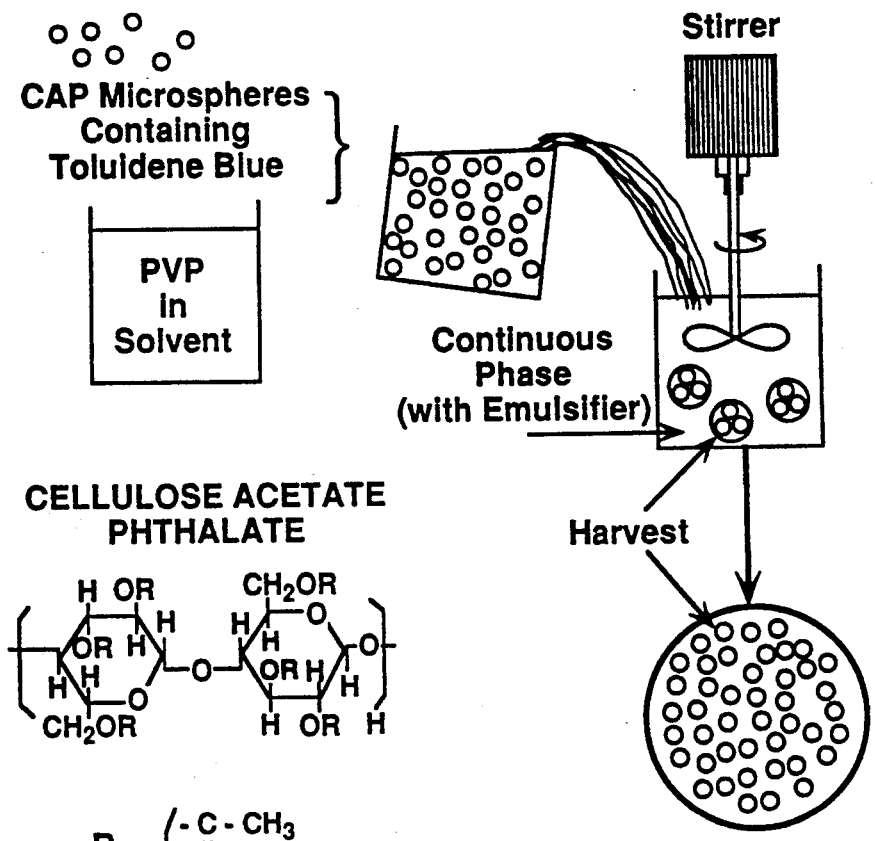
FIG. 5 shows how solvent evaporation technique was used to encapsulate CAP microspheres of 30-50 μm in PVP.
Figure 5:
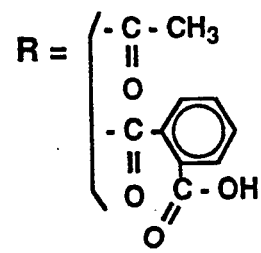
Figure 5:
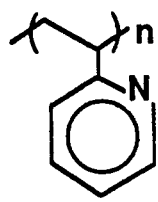

FIG. 4 shows the dye release from CAP microspheres at pH 1.45 and 7. At pH 1.45, dye release was minimal. However, at pH 7, the spheres were solubilized within 10 minutes.

This study demonstrated the ability of CAP microspheres to protect an encapsulated material. The microspheres released minimal amounts of dye while at simulated gastric pH (1.45), whereas the dye was released rapidly when placed in pH 7 solution.

EXAMPLE 9

Polyvinylpyridine (PVP) Coating of CAP Microspheres

For administering of microencapsulated materials to a human or animal, it can be desirable to incorporate CAP microspheres into food as a paste. Since food paste exposes microspheres to a pH range of 5.0–9.0, it is necessary to protect CAP from dissolving in pH higher than 5.0 by coating the microspheres with a water impermeable polymer. This polymer should be soluble in acidic pH to ensure solvation in the gastric region. We have found that polyvinylpyridine (PVP) can be used to coat the CAP microspheres. The PVP may be poly-2-vinylpyridine. Such double coating would be effective when administering a pediatric medicine. Aspirin and antibiotics are examples of such medicines. In a double coating of CAP and PVP, the microencapsulated material could be mixed with baby food and given orally without the enteric coating being too easily solubilized.

Three solvent systems were examined for PVP coating of CAP microspheres:
1. HCl (pH 1.0).
2. 15% acetone/methanol mixture.
3. Methylene Chloride.

Casting a film of CAP microspheres in a pH 1.0 HCl solution of PVP resulted in a sheet of coated CAP microspheres which could be broken down for administration. This procedure was not desirable since an unknown amount of CAP microspheres would be exposed due to powderization of the casted PVP sheet. Also, the slow rate of evaporation of HCl solution and the small yield of coated CAP hindered further pursuit of this procedure.

PVP was also dissolved in a mixture of 85% methanol and 15% acetone. however, this solvent system dissolved the microspheres as well. Regardless, a film was cast and the solvent evaporated quickly enough to leave some CAP microspheres intact. This film was introduced to acidic media (pH 1.0) and the PVP film dissolved within five minutes, leaving the CAP microspheres free-flowing. The pH was then raised to 7.5. PVP reprecipitated at once but did not interfere with CAP dissolving (within 10 minutes). Since an outline of reprecipitated PVP in the shape of CAP microspheres was left, the pH was reduced to 1.0, which left a clear solution. This removed doubts of residual CAP remaining unsolved. Therefore, the PVP protected the CAP microspheres at higher pH and did not interfere with solvation of the microspheres after reprecipitation.

Attempts to find a preferred solvent yielded methylene chloride.

Solvent evaporation:

1. Make 250 ml of 0.25% (w/v) solution of Airvol 205 (PVA, Air Products) in water.
2. Dissolve 0.8 g 200 kD PVP (oly-2-vinylpyridine, Aldrich) in 10 ml methylene chloride.
3. Add about 80 mg of CAP microspheres (30–50 μm diameter) and stir for five minutes.
4. While stirring the PVA solution at 400 rpm in a 400 ml beaker, the CAP/PVP suspension is added in a continuous narrow stream.
5. The emulsion is stirred for three hours.
6. Make a 1.0% (v/v) solution of TWEEN®20 in water adding one drop of ARLACEL™ 20 for every 1.0 ml of TWEEN®20 used.
7. After three hours, dilute the emulsion with the TWEEN®20 solution and vacuum filter the spheres washing excessively to remove the PVA.
8. Vacuum dry the cake.

By using the solvent evaporation technique, it is possible to suspend the CAP microspheres in the PVP solution (dissolved in methylene chloride) and emulsify this solution complex in water. After evaporation of the solvent (methylene chloride), the PVP coated CAP microspheres can be harvested for oral administration (see FIG. 4).

For this procedure an emulsifier was needed. PVA (polyvinyl alcohol) was chosen as the emulsifier. Elvanol 50-42 (du Pont) and Airvol 205 (Air Products) were used. The 0.25% Elvanol 50-42 solution resulted in major clumping. After several attempts changing different variables, the use of this emulsifier was stopped. After switching to Airvol 205, the quality of the emulsified phase was better, giving more uniform drop formation and much less clumping. The clumping was also reduced by using higher stirring rate (400 compared to 300 rpm) to keep the PVA wet. Methylene chloride has a solubility of 2 g/100 g water. This can be used to remove any residual solvent when harvesting by washing with excess volume of water. The optimum harvesting was done after three hours of stirring. Any less time could result in recombination of the PVP spheres due to the presence of solvent. Any longer period is unnecessary and could result in more clumping. It is believed that the clumping (mostly on the impeller) could be alleviated by using a teflon impeller. Harvesting the microspheres was difficult due to the adhesion of the PVP spheres to glass. Washing the microspheres with a 1% solution of TWEEN®20 and ARLACEL TM 20 prevented this problem. After vacuum drying the spheres, the few clumps present were easily broken to individual microspheres.

Some variables affecting this technique are as follows:
1. Airvol 205 proved to be the emulsifier with the best results (least amount of debris and aggregation).
2. By using higher rpms, clumping on the impeller can be reduced.
3. If the droplets are harvested before the solvent is completely evaporated, the droplets may recombine.
4. If PVA is removed too early, agglomeration will occur. If PVA is removed too late, the load (in this case, CAP) can be released into the aqueous (continuous) phase.

As described above, oral delivery of pH-sensitive proteins requires protection from gastric juices. Stomach upsetting agents (analgesics, etc.) have been enteric coated with polymers such as cellulose acetate phthalate (CAP). However, these require extensive formulation development into tablets and syrups which are undesirable and hard to administer to infants. With the double encapsulation technique of the subject invention, tasteless, water-impermeable microspheres can be incorporated into baby food. The outer poly-2-vinylpyridine layer is stable at higher pH, but will dissolve in gastric juices, releasing the CAP microspheres containing the drug. In turn, CAP microspheres will release their contents in the intestine.

EXAMPLE 10

Dye Release from PVP-Coated CAP Microspheres

Dye release from PVP-coated CAP microspheres in several solutions of different pH was tested. The microspheres were put through the following stages:
1. Microspheres were placed in a pH 8 solution. Solution was removed after 15 minutes.
2. A pH 2 HCl solution was added and removed after 20 minutes.
3. A solution of pH 1.1 was added for 15 minutes.
4. In the final stage the microspheres were put in pH 8 solution.

No change in the appearance of the PVP microspheres was observed after introducing them to the pH 8 solution. In pH 2, PVP microspheres showed a very slow release of CAP microspheres. After 20 minutes, the majority of the spheres were intact. When pH 1.1 solution was added, much faster rate of dissolution was observed. All the PVP microspheres dissolved after 15 minutes, releasing the CAP microspheres which exhibited no dye release at this stage. CAP microspheres were totally dissolved within five minutes after placing the microspheres in pH 8 solution, releasing the dye, which in turn colored the reprecipitated PVP crystals.

The microspheres were placed in a simulated process of emulating the food paste (pH as high as 8), the gastric region (pH 1-2, fasted), intestines (pH 6.5-8.0). The PVP protected the CAP spheres from dissolving in a pH 8 solution. Afterwards, slow release of CAP microspheres was observed at pH 2. A faster CAP release was exhibited at pH 1.1 with all PVP spheres dissolving after 15 minutes. At this pH the CAP microspheres were intact with the dye incorporated, which suggests they would have protected the active ingredient after being released. When pH was changed to 8, the CAP microspheres dissolved, releasing the dye (MB), which in turn colored the reprecipitated PVP crystals. Therefore, the system functioned properly.

EXAMPLE 11

Enzyme Activity Studies

Studies were conducted using fresh *Oxalobacter formigenes* encapsulated in alginate as described in Example 2. The activity of the fresh bacteria was determined to be about 71.1 nmole/min.mg (average of two runs: 70.8 and 71.4 nmole/min.mg, respectively). This result was repeated using varying amounts of bacteria.

We incubated samples of encapsulated bacteria at 37° C. for long-term study. Some samples showed signs of contamination (no preservative was used); however, uncontaminated microcapsules showed a 40% activity after two months and 10% activity after four. These activities are in a range where they can degrade a normal oxalate load in vivo ($\approx$40 mg/day, Hodgkinson [1977], supra).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. In a method for preparing microcapsules of cells, viruses, drugs, or polypeptides, wherein said method comprises the following steps:
    (a) mixing said cells, viruses, drugs, or polypeptides with a matrix-forming composition;
    (b) making droplets of the mixture of part (a) and introducing said droplets into a gelling solution to form gel droplets;
    (c) treating the gel droplets formed in part (b) with a polyelectrolyte to form a microcapsule;
an improvement which comprises making droplets in part (b) which have a size of between about 40 µm to about 100 µm and modulating the electrical characteristics of the surface said droplets before introducing said droplets into said gelling solution.

2. The method, according to claim 1, wherein said matrix-forming composition comprises alginate.

3. The method, according to claim 2, wherein said electrical charge is imparted onto said droplets by passing said droplets through an electrical field created by a tesla coil.

4. The method, according to claim 3, wherein said droplets are passed through an O-ring wherein said O-ring is attached to a tesla coil.

5. The method, according to claim 2, wherein said gelling solution is a calcium chloride solution which further comprises a surfactant.

6. The method, according to claim 5, wherein said droplets enter said calcium chloride solution from a depth of about 9 cm.

7. The method, according to claim 6, which further comprises adding at least one additional layer of alginate to said microcapsule by dipping said microcapsule into an alginate solution wherein said alginate solution has a concentration of approximately 10% of the concentration of the alginate solution used in part (a).

8. The method, according to claim 1, wherein said polyelectrolyte is poly-L-lysine.

9. The method, according to claim 8, which comprises adding 3 additional layers of alginate and 3 additional layers of poly-L-lysine with an alginate layer being the last to be added.

10. The method, according to claim 9, which further comprises a liquefaction step.

11. The method, according to claim 10, wherein said liquefaction step comprises treatment with citrate.

12. The method, according to claim 11, wherein said citrate treatment is with a 1.5% citrate solution for at least 5 minutes.

13. The method, according to claim 12, wherein said encapsulated material is selected from the group consisting of bacteria, peptides and islet cells.

14. The method, according to claim 13, wherein said bacteria are *Oxalobacter formigenes*.

15. The method, according to claim 2, wherein said gelling solution is a calcium chloride solution.

16. A microcapsule produced by the process of claim 1.

17. A microcapsule comprising an active ingredient encapsulated by two distinct layers wherein a first layer is comprised of a first composition which is not significantly soluble in pHs of less than about 3.0 and wherein a second layer is comprised of a second composition which is not significantly soluble in pHs between about 6.0 and about 8.0; wherein said second layer surrounds said first layer and wherein said first layer surrounds said active ingredient.

18. The microcapsule, according to claim 17, wherein said first composition is cellulose acetate phthalate and wherein said second composition is polyvinylpyridine.

19. The microcapsulate, according to claim 17, wherein said active ingredient is selected from the group consisting of aspirin and antibiotics.

* * * * *

UNITED STATES PATENT AND TRADEMARK OFFICE
CERTIFICATE OF CORRECTION

PATENT NO. : 5,286,495
DATED : February 15, 1994
INVENTOR(S) : Chris Batich, et. al.

It is certified that error appears in the above-indentified patent and that said Letters Patent is hereby corrected as shown below:

Column 18  line 25: Delete "The microcapsulate," and insert --The microcapsule--.

Column 14  line 45: Delete "(oly-2-vinylpyridine" and insert --(poly-2-vinylpyridine--.

Signed and Sealed this

Nineteenth Day of July, 1994

*Attest:*

BRUCE LEHMAN

*Attesting Officer*     Commissioner of Patents and Trademarks